US008383333B2

(12) United States Patent
Maki et al.

(10) Patent No.: US 8,383,333 B2
(45) Date of Patent: Feb. 26, 2013

(54) HBV PRECORE PROTEIN CAPABLE OF FORMING PARTICLES

(75) Inventors: Noboru Maki, Wako (JP); Tatsuji Kimura, Wako (JP); Shintaro Yagi, Wako (JP)

(73) Assignee: Advanced Life Science Institute, Inc., Saitama (JP)

(*) Notice: Subject to any disclaimer, the term of this patent is extended or adjusted under 35 U.S.C. 154(b) by 422 days.

(21) Appl. No.: 12/654,280

(22) Filed: Dec. 16, 2009

(65) Prior Publication Data

US 2010/0285444 A1 Nov. 11, 2010

Related U.S. Application Data

(62) Division of application No. 10/526,744, filed as application No. PCT/JP03/11389 on Sep. 5, 2003, now Pat. No. 7,713,532.

(30) Foreign Application Priority Data

Sep. 6, 2002 (JP) ................................. 2002-261666

(51) Int. Cl.
*C12Q 1/70* (2006.01)
*G01N 33/53* (2006.01)
(52) U.S. Cl. ............................................ 435/5; 435/7.1
(58) Field of Classification Search .................... None
See application file for complete search history.

(56) References Cited

FOREIGN PATENT DOCUMENTS

| WO | WO 01/40279 A2 | 6/2001 |
| WO | WO 02/14871 | * 2/2002 |
| WO | WO 02/14871 A1 | 2/2002 |

OTHER PUBLICATIONS

GenBank Accession No. AAD41100, Jun. 28, 1999, 1 page.
Beterams et al., "Packaging of up to 240 subunits of a 17 kDa nuclease into the interior of recombinant hepatitis B virus capsids", FEBS Letters, 2000, vol. 481, No. 2, pp. 169-176.
Birnbaum et al., "Hepatitis B Virus Nucleocapsid Assembly: Primary Structure Requirements in the Core Protein", Journal of Virology, 1990, vol. 64, No. 7, pp. 3319-3330.
Chang et al., "Impact of hepatitis B vaccination on hepatitis B disease and nucleic acid testing in high-prevalence populations," J. Clin. Virol., 2006, 36(Supp. 1):S45-S50.
Database UniProt, Nov. 1, 1996, XP-002378531, Database Accession No. Q89714.
Kimura, Tatsuji et al., "Sensitive Enzyme Immunoassay for Hepatitis B Virus Core-Related Antigens and Their Correlation to Virus Load", *Journal of Clinical Microbiology*, Feb. 2002, vol. 40, No. 2, pp. 439-435.
Kimurai et al., "Hepatitis B Virus DNA-negative Dane Particles Lack Core Protein but Contain a 22-kDa Precore Protein without C-terminal Arginine-rich Domain", The Journal of Biological Chemistry, 2005, vol. 280, No. 23, pp. 21713-21719.
Kobayashi et al., "Complete nucleotide sequence of hepatitis B virus DNA of subtype adr and its conserved gene organization," Gene, 1984, 30:227-232.
Milich et al., "The Hepatitis Nucleocapsid as a Vaccine Carrier Moiety", Annals of the New York Academy of Science, 1995, vol. 754, pp. 187-201.

(Continued)

*Primary Examiner* — Shanon A Foley
(74) *Attorney, Agent, or Firm* — Foley & Lardner LLP (57) ABSTRACT

There is provided a HBV precore protein having an ability of forming particles, and a means for determining it. A novel HBV precore protein that forms the virus (like) particles of HBV was identified. The present invention provides this novel HBV precore protein. Furthermore, there are provided core-like particles and virus-like particles formed by this HBV precore protein. These virus-like particles can be used for vaccines and therapeutic agents. The present invention also provides a method of determining the HBV precore protein and a method of determining the anti-HBV precore protein antibody.

5 Claims, 6 Drawing Sheets

OTHER PUBLICATIONS

Miyanohara et al., "Expression of hepatitis B virus core antigen genein *Saccharomyces cerevisiae*: synthesis of two polypeptides translated from different initiation codons," J. Virol., Jul. 1986, 59(1):176-180.

Nassal, "Novel molecular approaches toward therapy of chronic hepatitis B", Archives of Virology, 1997, vol. 142, No. 3, pp. 611-628.

Nassal, Michael et al., "An Intramolecular Disulfide Bridge between Cys-7 and Cys61 Determines the Structure of the Secretory Core Gene Product (e Antigen) or Hepatitus B Virus", *Journal of Virology*, Jul. 1993, vol. 67, No. 7, pp. 4307-4315.

Ou et al., "Comparative studies of hepatitis B virus precore and core particles," Virology, 1990, 174:185-191, abstract only.

Sakamoto, Y. et al., "Full and Empty Particles of Hepatitus B Virus in Hepatocytes from Patients with HBsAg—Positive Chronic Active Hepatitus", *Laboratory Investigation*, 1983, vol. 48, No. 6, pp. 678-682.

Schlicht et al., "The Quaternary Structure, Antigenicity, and Aggregational Behavior of the Secretory Core Protein of Human Hepatitis B Virus are Determined by Its Signal Sequence", Journal of Virology, 1991, vol. 65, No. 12, pp. 6817-6825.

Schodel et al., "Hepatitis B virus core and e antigen: immune recognition and use as a vaccine. carrier moiety," Intervirology, 1996, 39:104110.

Takahashi, K. et al., "Molecular Heterogeneity of e Antigen Polypeptides in Sera From Carriers of Hepatitis B Virus", *The Journal of Immunology*, Nov. 1991, vol. 147, No. 9, pp. 3156-3160.

Terre, S., et al., "Defective Hepatitis B Virus Particles are Generated by Packaging and Reverse Transcription of Spliced Viral RNAs In Vivo", *Journal of Virology*, Oct. 1991, vol. 65, No. 10, pp. 5539-5543.

Ulrich et al., "Core Particles of Hepatitis V Virus as Carrier for Foreign Epitopes", Advances in Virus Research, 1998, vol. 50, pp. 141-182.

Wasenauer, et al., "A Cysteine and a Hydophobic Sequence in the Noncleaved Portion of the Pre-C Leader Peptide Determine the Biophysical Properties of the Secretory Core Protein (HBe Protein) of Human Hepatitis B Virus", Journal of Virology, 1992, vol. 66, No. 9, pp. 5338-5346.

* cited by examiner

HBV PRECORE PROTEIN CAPABLE OF FORMING PARTICLES

CROSS-REFERENCE TO RELATED APPLICATIONS

This application is a Divisional of U.S. application Ser. No. 10/526,744, which is the U.S. National Stage application of PCT/JP03/11389, filed Sep. 5, 2003, which claims priority from Japanese application JP 2002-261666, filed Sep. 6, 2002.

TECHNICAL FIELD

The present invention relates to a HBV precore protein capable of forming core-like particles.

BACKGROUND ART

Diagnosis of viral infections can be made by methods of detecting viruses or virus-related components (proteins and nucleic acids), and methods of determining specific antibodies produced by living organisms due to viral infection. In the infection of the hepatitis B virus (HBV), diagnostic markers such as HBs antigen and antibody, HBc antibody, HBe antigen and antibody, and HBV-DNA have been introduced in laboratory tests.

Generally, the presence of HBV infection can be known by the HBs antigen or the HBc antibody. Not only for infectivity of HBV but as indices for judging pathology and prognosis of HBV carriers, and therapeutic effects, determinations of HBe antigen and antibody and the amount of HBV-DNA have been used. Due to its simple and inexpensive procedures, immunological measurement of HBe antigen and antibody, among them, has been most widely used. In precore mutants that cannot produce or secrete HBe antigen, however, there are cases in which the propagation of HBV is active, infectivity and immunogenicity are potent, and pathology is active though HBe antigen is negative. On the other hand, regardless of whether they are wild types or mutants, the measurement of the amount of HBV-DNA that reflects the propagation and replication state of HBV is important, but it has problems that the procedures of pre-treatment and measurement are complicated, and lack reproducibility and stability.

Recently, a method of determining HBV core-related antigens was developed that is thought to reflect the propagation and replication state of HBV despite the presence of HBV core-related antibodies (HBC antigen and HBe antibody) or the appearance of mutants. Kimura et al. (Journal of Clinical Microbiology, 40:439-445, 2002) have developed an immunoassay that simultaneously detects HBc antigen and HBe antigen in the serum by a simple pre-treatment using a monoclonal antibody having a specificity for the HBV core-related antigens (HBV precore/core gene products containing HBc antigen and HBe antigen), and have demonstrated that it has a correlation with the NAT testing method that detects the virus genome.

According to the literature so far, the HBV precore/core gene encodes a protein comprising a full-length of 212 amino acid residues (amino acid Nos. −29 to 183, when the first amino acid of the HBc antigen was set as 1. The same holds true hereinafter), and has a signal peptide of 19 residues at the N-terminal thereof. The signal peptide comprises hydrophobic amino acid residues and functions as a signal sequence for the protein secreted to bind to the membrane. Here, it represents a sequence comprising amino acids at -29 to −11.

The precore protein, when translated, passes through the endoplasmic reticulum membrane and, after cleaving the 19-residue signal peptide, the C-terminal nucleic acid-binding domain is cleaved to become the HBe antigen (amino acid Nos. −10 to 149), which is secreted into the blood. This HBe antigen was conventionally thought to occur in association with serum proteins such as albumin and γ-globulin in the blood, and it had not been reported to form HBV particles. There are also some reports that HBe antigen is involved in the maintenance of immunological tolerance, suppression of virus replication etc., but it is not indispensable for HBV replication, and there is much to be elucidated on its biological role.

HBV precore/core gene has the second transcription initiation signal, and a product transcribed and translated from this signal turns into the HBc antigen (amino acid Nos. 1-183), which, while incorporating HBV pregenome RNA, forms a virus capsid and is coated with an outer coat (envelope) comprising HBs antigen and, then, is extracellularly released as complete virus particles (Dane particles). It has been reported that when the amino acids at positions 1-144 among the HBc antigen are present, core particles are formed and the molecule forming the core particles of the infectious virus are believed to be comprised of a protein having an amino acid sequence at positions 1-183.

Though HBc antigen and HBe antigen are proteins that share the majority of the sequences, they have significantly different properties. Significantly responsible for this difference is a cysteine residue of the amino acid at position −7 of the HBe antigen. This cysteine, in combination with the cysteine residue at amino acid position 61 in the same molecule, forms a disulfide bond and acquires the properties of e antigen (M. Nassal and A. Rieger, Journal of Virology, 67: 4307-4315, 1993). The fact that when, for example, the cysteine at position −7 is replaced with another amino acid to prevent the disulfide bond from forming, the conformation of HBe antigen is not taken also indicates the significance of this disulfide bond.

On the other hand, as HBc antigen is transcribed and translated from the amino acid at position 1, it does not have the cysteine residue at position −7 and thus takes the HBc conformation, and two molecules of HBc protein turn into a homodimer by forming a disulfide bond between the cysteine residues at amino acid position 61, thereby forming a virus capsid (core particles).

The HBV core-related antigens occurring in the serum of HBV patients are roughly divided into the HBc antigen (amino acid Nos. 1-183) that constitutes the infectious Dane particle and the secretary HBe antigen (amino acid Nos. −10 to 149) that is almost the same as the HBc antigen in terms of amino acid sequence but has an antigenicity different from that of the HBc antigen. However, in addition to the above, the presence of pre-HBe antigen (amino acid Nos. −29 to 149) in the blood that exhibits a HBe antigenicity as a minor molecule has been demonstrated by Takahashi et al. (Journal of Immunology, 147, 3156-3160, 1991).

They separated the pooled sera by centrifugation, and purified from the supernatant a protein having a HBe antigenicity using an affinity column of anti-HBe monoclonal antibody and sequenced it. As described above, the HBe antigen protein is thought to occur in the blood without forming virus particles. They also have decided the HBe antigen sequence that was purified without peeling off (disrupting) the HBs antigen which is a coat protein of HBV or without disrupting virus particles and core particles, and the HBe antigen having the signal sequence (amino acid Nos. −29 to 149) demonstrated by them is believed to occur in a free state in the serum.

On the other hand, it has been reported that, among Dane particles, there are some empty particles containing no HBV-DNA (SAKAMOTO et al., Laboratory Investigation, 48, 678-682, 1983) or replication-defective deficient particles containing shorter-than-usual HBV-DNA that underwent splicing (TERRE et al., Journal of Virology, 65, 5539-5543, 1991), but the HBV protein constituting the particle has not been analyzed in detail.

Thus, biochemical characterization of the HBV core-related antigens analyzed in the above literature cannot be considered sufficient, and the form of the HBV core-related antigens as virus markers in the blood that is thought to reflect the state of propagation and/or replication of HBV has not been resolved yet.

DISCLOSURE OF THE INVENTION

Among the clinically significant NAT testing of HBV, there are currently the PCR method and the TMA method, but the problems associated therewith are the high cost and the complicated procedure of testing. Also, as a genetic amplification method is used, primers for amplification incompatible with the target DNA may cause false negatives. On the other hand, immunoassay is simple and inexpensive to perform, but the current method of determining HBe antigen as a propagation marker cannot determine HBe antigen present as an immune complex in the presence of HBe antibody, and precore mutants and core promoter mutants that cannot produce and secrete HBe antigen test negative for HBe antigen. In addition, methods of determining HBc antigen, though it correlates with the amount of HBV-DNA, is complicated in procedure and it is not sensitive enough, and thereby it has not been put into clinical application.

Thus, it is an object of the present invention to biochemically characterize HBV core-related antigens for possible clinical applications such as screening of type B hepatitis and monitoring in the treatment of patients with chronic type B hepatitis, and to identify molecular species of HBV core-related antigens in the blood that reflect the propagation and replication state of HBV.

Such characterization as above will lead to the discovery of molecular species useful for diagnosis etc. of HBV-infected patients and the development of new diagnostic reagents.

Also, the analysis of the form of HBV core-related antigens present and its role can lead to the development of new HBV vaccines and therapeutic agents.

According to the present invention, HBV particles and HBV related proteins in the blood were subjected to sucrose density gradient centrifugation, ELISA, electrophoresis etc. to separate and purify HBV core-related antigens, and antigens different from the conventionally reported HBe antigen or HBc antigen were isolated, and a novel molecule forming core-like particles was identified by mass spectrometry. One aspect of the present invention is to provide an HBV precore protein containing all or part of the signal sequence capable of forming virus-like particles.

As used herein, a part means a sequence comprising one residue or more from the N-terminal end of the 19-residue signal sequence. The C-terminal of this HBV precore protein is one obtained by cleaving the protein at one of the RRRGR at amino acid position 150 or after. Furthermore, this may contain mutations in the signal sequence or the HBe sequence portion (amino acid Nos. −10 to 149), which may be any mutation as long as they can form core-like particles. Most preferably, this HBV precore protein is a polypeptide comprising the amino acid sequence as set forth in SEQ ID NO: 1.

The present invention further provides HBV core-like particles or HBV virus-like particles comprising the above HBV precore protein.

The present invention also provides a HBV diagnostic reagent or a kit comprising this HBV precore protein, or the HBV core-like particles or the HBV virus-like particles composed of this protein.

The present invention also provides a method, a diagnostic reagent, or a diagnostic kit for determining this HBV precore protein.

The method of determining this HBV precore protein may include the step of exposing the HBV precore protein, and of allowing the HBV precore protein to bind to the probe recognizing it. The step of exposing the HBV precore protein may treatment with or the addition of a surfactant. The effective surfactants include, but are not limited to, nonionic surfactants, and specifically anionic surfactants are preferred. Also effective are those in which an ampholytic surfactant has been added to an anionic surfactant, and those in which a nonionic surfactant has been further added to the above.

Furthermore, the probe that binds to the above HBV precore protein may be a probe that binds to the sequence of amino acid Nos. −28 to −11. This probe may be an antibody.

Also, only the HBV precore/core protein that was made free of free HBe antigen can be specifically determined by immunoprecipitating with anti-HBs antibody and determining the HBV precore/core protein in the precipitate. This immunoprecipitation can be replaced with a separation method that employs a probe that binds to HBs antigen.

When the above determined value of the HBV precore protein includes that of HBe antigen, the value of the particulate HBV precore protein in the sample can be calculated and determined by subtracting the value of HBe antigen. Furthermore, it is also possible to determine the exact value of the particulate HBV precore protein in the sample by subtracting the value of HBc antigen therefrom. The determined quantitative value of the particulate HBV precore protein can be used as a pathological marker for HBV infection.

Furthermore, the present invention provides an assay kit comprising an anionic surfactant and an antibody that recognizes amino acids at positions −28 to 150 of the HBV precore protein, and a diagnostic reagent comprising said kit for determining HBe antigen.

In another embodiment, the present invention provides a HBV vaccine and a therapeutic agent comprising the HBV precore protein.

In addition, the present invention provides a method, or a diagnostic reagent and a diagnostic kit for determining an antibody against the particulate HBV precore protein.

These can use the above HBV precore protein particles as the antigen. The particles can be obtained from the serum etc. by purifying with density gradient centrifugation, immunoprecipitation and the like, and the HBV precore protein antigen can be exposed by removing the envelope with a surfactant etc. It is also possible to produce the particulate HBV precore protein by recombinant protein.

Using this antigen, an antibody against the particulate HBV precore protein different from HBc antibody or HBe antibody can be determined.

BEST MODE FOR CARRYING OUT THE INVENTION

The present invention will now be explained in detail below.

The HBV precore protein newly identified in the present invention is a protein that contains the signal sequence and that can form virus-like particles of HBV. The major molecule of the inventive protein in the blood is the p22 antigen with a molecular weight of 22000 Daltons. A representative amino acid sequence of the p22 antigen is an antigen that comprises 178 amino acids as set forth in SEQ ID NO: 1 and that is similar to the HBV precore antigen. By obtaining an antibody that specifically recognizes this antigen and then by combining this with a sample pretreatment method to construct an assay system, the HBV core-related antigens can be determined even in the presence of the antibody.

The so-called HBV precore/core protein comprises HBe antigen (HBV e protein), HBc antigen (HBV core protein) and other HBV precore/core gene products. As used herein "HBV precore protein" indicates, unless otherwise specified, a protein product of the HBV precore/core gene having the signal sequence and an ability of forming particles. Its representative protein is the protein described in the sequence listing 1. Also, "HBV core-related antigen" indicates a HBV precore/core gene product comprising HBc antigen (HBV core protein) and HBe antigen (HBV e protein).

First, when the serum of a patient with type B hepatitis was fractionated by sucrose density gradient centrifugation and the HBV core-related antigen in each fraction were determined, a peak at a density of about 1.05 at almost the same fraction as HBs antigen, and another peak at a density of about 1.17 at almost the same fraction as HBc antigen and HBV DNA could be detected. Furthermore, refractionation of the peak at a density of about 1.17 by sucrose density gradient centrifugation at a low gradient revealed that the HBc antigen and HBV DNA exhibited peaks at the same fraction whereas the HBV core-related antigen exhibited a peak at a slightly lower density fraction at which fraction HBs antigen, a coat protein of the virus, can be detected.

Thus, in the serum of patients with type B hepatitis, virus-like particles comprising the HBV core-related antigen having a slightly smaller density are thought to occur in addition to the infectious Dane particles.

Also, when the fraction containing the particles comprising the HBV core-related antigen and the fraction containing Dane particles are subjected to gel filtration, particles comprising HBc antigen and HBV core-related antigen are each eluted in the void fraction. When the same fractions are treated with Nonidet P-40 (NP-40: Nacalai Tesque Inc.), the coat protein HBs antigen is peeled off, and then subjected to gel filtration, particles comprising HBc antigen and HBV core-related antigen are also each eluted in the void fraction. This indicates that each of the particles comprising HBc antigen and HBV core-related antigen forms a structure that is robust enough to withstand the surfactant treatment that peels off the coat protein HBs antigen.

Then, the analysis using the Western blotting method has shown that the HBV core-related antigen exhibits a molecular weight of about 22,000 Daltons which is almost the same as that of HBc antigen, but it does not react to a monoclonal antibody (HB50) specific for the C-terminal nucleic acid-binding region carried by HBc antigen. Thus, based on its molecular weight, this HBV core-related antigen is thought to contain no C-terminal nucleic acid-binding region and is the product (p22 antigen) of the precore gene in which the signal sequence has not been cleaved.

When the p22 antigen, after being separated by the SDS-PAGE method, is excised from the polyacrylamide gel and its amino acid sequence is analyzed by the matrix-assisted laser desorption/ionization (MALDI) mass spectrometry (Carr et al., Current Protocols in Molecular Biology, John Wiley & Sons, Inc., New York Units, 1997), the p22 antigen was demonstrated to be a HBV precore protein comprising 178 amino acids as set forth in SEQ ID NO: 1.

This amino acid-sequenced HBV core-related antigen is designated hereinafter as the HBV precore protein.

The HBV precore protein of the present invention, when compared to the HBV precore protein (pre HBe antigen) previously reported by TAKAHASHI et al. (Journal of Immunology, 147, 3156-3160, 1991), lacks methionine at the N-terminal (position −29) and the glutamine at position −28 has been acetylated. At the C-terminal end, arginine has been bound to valine at position 149 which is the C-terminal of HBe antigen, and amino acids are present at least up to position 150. As this HBV precore protein is not recognized by the monoclonal antibody HB50 that recognizes a region containing SPRRR (SEQ ID NO: 7) among the HBV nucleic acid-binding site, it is likely to contain amino acids up to position 154.

As the HBV precore protein of the present invention forms incomplete virus particles (virus-like particles), it can be easily estimated that this protein competes with HBc antigen in capsid formation and thereby inhibits virus replication. Thus the present invention provides a possibility of a therapeutic agent for HBV using the HBV precore protein.

The HBV precore protein of the present invention forms HBV virus-like particles in the body of HBV-infected patients. The present invention also suggests that this HBV precore protein is present in the intact HBV virus particles. Thus, it is believed that the HBV precore protein forms the HBV nucleocapsid together with HBc antigen. Therefore, the measurement of this HBV precore protein is thought to serve as a marker for diagnosis of HBV infection and for diagnosis of the pathogenesis of hepatitis and hepatic cirrhosis or hepatic cancer.

The HBV precore protein of the present invention has different functions and a different amino acid sequence from those of HBe antigen or HBc antigen. However, because of the overlapping of functionally similar properties and amino acid sequences, this HBV precore protein must be determined differentially from HBe antigen or and HBc antigen. It is to be noted that the amount ratio of this HBV precore/core protein to HBc antigen is 12:1 to 158:1, or the difference of at least 12-fold as shown in Example 7.

The difference of the HBV precore protein of the present invention and HBe antigen or the HBe antigen that has the signal peptide as reported by Takahashi et al. is that the former is functionally forming the core-like particles (virus-like particles) of HBV whereas the latter in a free state is associated with serum proteins in the blood. As to the function of forming core-like particles (virus-like particles), this HBV precore protein and HBc antigen share almost the same functions. As this HBV precore protein has a property of forming particles, it is estimated to have a structure closer to HBc antigen than to HBe antigen, and thus it is thought that no disulfide bonds have been formed between the amino acid cysteine at position −7 and cysteine at position 61.

When the HBV core-related antigen (HBV precore/core protein) detected by the HBV core-related antigen assay system, as shown in Example 9 below, was determined by the conventional HBc antigen assay method or the HBe antigen assay method, no HBc antigen or HBe antigen was detected. This is thought to indicate the following: (1) The HBV core-related antigen contains much of the HBV precore protein of the present invention; (2) Some of the conventionally obtained antibodies that bind to HBc antigen or HBe antigen do not bind to the HBV precore protein, and thus the antigenicity of the HBV precore antigen is different from that of HBc antigen or HBe antigen.

This indicates that the HBV precore protein of the present invention had hardly been detected by the conventional HBc antigen assay method or the HBe antigen assay method. In other words, it can be said that the measurement was realized for the first time by the HBV core-related antigen assay method of Kimula et al. The HBV precore protein can be detected by the HBV core-related antigen assay method. The characteristics of this assay method is that samples containing the HBV precore protein are treated with a surfactant, and then reacted to the antibody in the presence of a surfactant. Accordingly, it is necessary that antigen epitopes on the HBV precore protein must be stable in the presence of the surfactant. The antibody used must also be functionally stable in the presence of the surfactant.

As epitopes recognized by the antibody, linear epitopes of amino acids at positions 1-19, 21-40, 31-49 and 131-140, and structural epitopes of amino acids at positions 1-81 are suitable. Combination of antibodies that recognize these epitopes made possible the measurement of the HBV precore protein. By combining two or more antibodies that recognize these epitopes, the HBV precore protein can be detected and specifically preferred are combinations of antibodies that recognize epitopes of amino acids at positions 21-40 and 31-49, 1-19 and 21-40, 21-40 and 31-49, and the addition of an antibody that recognizes another epitope to the above combination leads to increased sensitivity.

The antibody for use in detection must be able to bind to the above epitope in the presence of a surfactant. As the surfactant for use in the measurement of the HBV precore protein, an anionic surfactant is preferred, but the combination of an anionic surfactant and an ampholytic surfactant, or the combination of an anionic surfactant, an ampholytic surfactant and a nonionic surfactant further increases sensitivity. While SDS was most suitable among the anionic surfactants, other anionic surfactants are also effective, and by replacing SDS with another structurally similar anionic surfactant, the above epitope of the HBV precore protein can be exposed so as to enable it to bind to the antibody.

Figure 1:
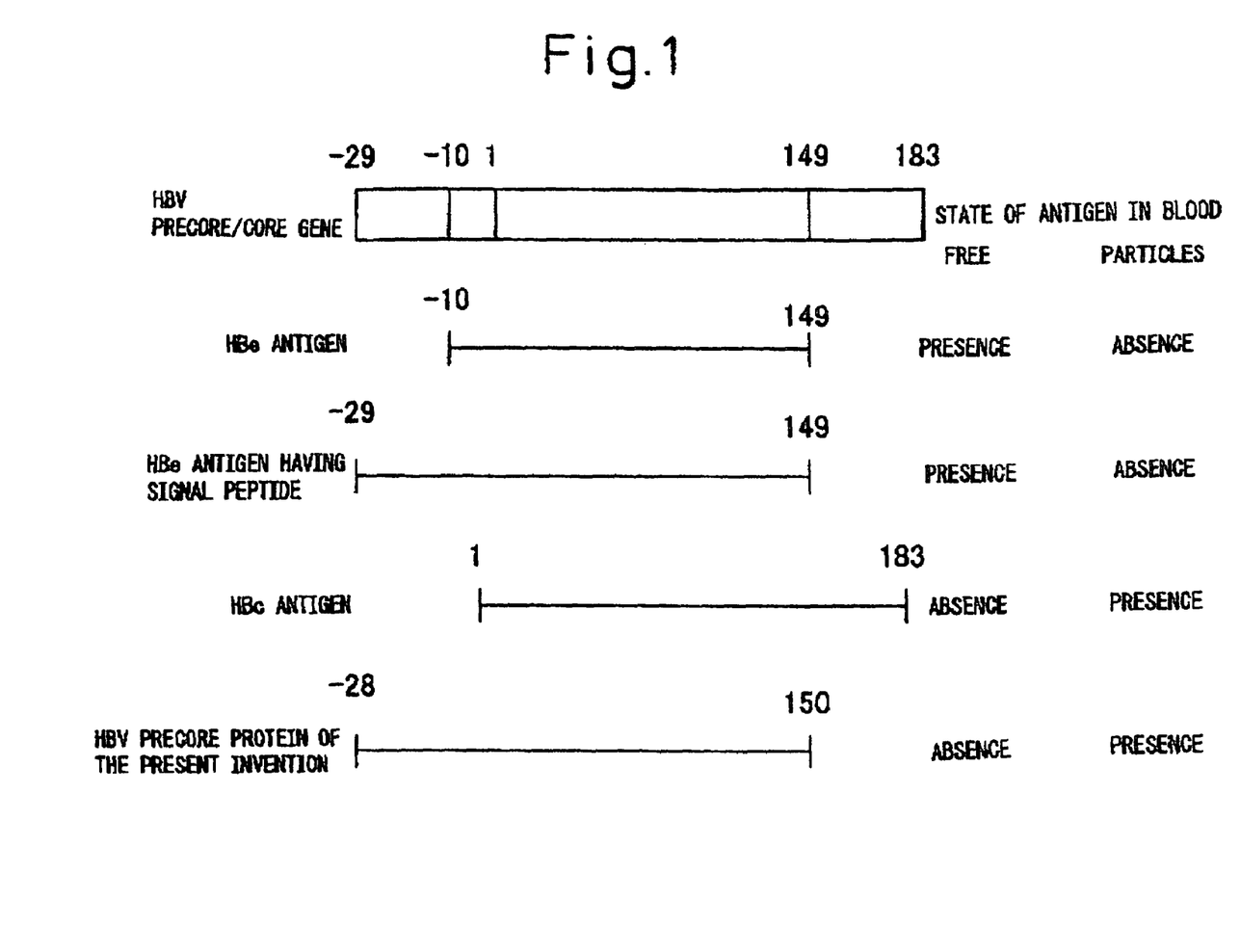
FIG. 1 is a drawing that shows the amino acid region of the HBV precore protein, HBe antigen, HBe antigen having the signal sequence and HBc antigen, and the state of each antigen in the blood.

Differences in the amino acid sequence among the HBV precore protein of the present invention and the known HBe antigen, the HBe antigen having the signal peptide reported by Takahashi et al., and HBc antigen are shown in FIG. 1. According to the present invention, the HBV precore/core protein is more likely to be represented by a polypeptide comprising an amino acid sequence at positions −28 to 150. In contrast, HBe antigen is composed of an amino acid sequence at positions −10 to 149, the HBe antigen having the signal sequence is composed of an amino acid sequence at positions −29 to 149, and HBc antigen is composed of an amino acid sequence at positions 1 to 183.

From the foregoing, though it is not easy to determine separately the HBV precore protein of the present invention and HBe antigen, the HBe antigen having the signal sequence and HBc antigen, it is possible to separate them using the function of whether or not the virus (like) particles can be formed and the difference in the amino acid sequences.

Firstly, in order to separate the HBV precore protein of the present invention and HBe antigen or the HBe antigen having the signal sequence, the characteristics that this HBV precore protein is forming HBV-like particles and that HBe antigen or the HBe antigen having the signal sequence is present in the free form (in this application, the HBe antigen that is binding to the antibody is considered to be free) are utilized. In practice:

(1) There is a method that the value measured prior to the treatment of disrupting virus particles and the value measured after the treatment of disrupting virus particles are compared. Thus, measurement can be effected by subtracting the value measured prior to the treatment of disrupting virus particles from the value measured after the treatment of disrupting virus particles.

(2) There is also a method that virus (like) particles are separated and the HBV precore protein contained therein is determined. As a method of separating the virus (like) particles, there can be mentioned a method of separating the fraction of the free antigen and the fraction forming the virus (like) particles by density gradient centrifugation, in which the HBV precore/core protein in the fraction in which virus (like) particles are contained is measured. In addition to the method of separating the free antigen and the virus (like) particles by density gradient centrifugation, a method of specifically concentrating virus-like particles or a method of specifically separating the free antigen is used, and after separation the amount of HBV precore/core protein can be determined.

As an example of such methods, there can be mentioned an immunoprecipitation method using an anti-HBs antibody. It is also possible to specifically determine only particulate HBV precore/core protein free of HBe antigen by determining the HBV precore/core protein in the precipitate.

Since the HBV precore protein and HBc antigen are similar in the function of forming core (like) particles (virus (like) particles), a method is possible in which different probes that specifically bind to (recognize) the different parts of the constituting amino acid sequence are used in order to determine them separately. Thus, in order to selectively determine the HBV precore protein, a probe that binds to amino acids at positions −29 to −10 may be used, and in order to selectively determine HBc antigen, a probe that binds to amino acids at positions 151 to 183 may be used.

Also, by using a probe that binds to both of them, the amount of the HBV precore protein+HBc antigen can be determined, and then by specifically determining either (protein) of the antigens and subtracting it, the amount of each antigen (protein) can be determined.

In fact, for the measurement of the HBV precore protein in the sample, the step of disrupting virus-like particles to expose the HBV precore protein is necessary. In this step, HBs antigen, a coat protein of the virus, is peeled off, and a treatment agent is used to liberate the HBV precore protein. The method of treatment includes an alkaline treatment in which the treatment with NaOH peels off HBs antigen off to liberate the antigen in the inside of HBV. As another treatment agent, a surfactant can be used, and a nonionic surfactant such as Triton X-100 and Nonidet P-40 and an anionic surfactant such as SDS and sodium sarcosine are suitable. Furthermore, combinations of an anionic surfactant as disclosed in Patent No. 3171827 and another surfactant are also effective.

If the measurement with a probe that recognizes an amino acid sequence at positions −29 to 149 is performed without the step of disrupting the virus-like particles and of exposing the HBV precore protein, free HBe antigen and the HBe antigen having the signal peptide are also measured. Thus, when the antigen protein in the sample was measured without separating the free antigen and the virus-like particles, the measured value obtained with treatment by a surfactant etc. from which the measured value of the HBe antigen without treatment by a surfactant was subtracted will be the measured value of the particulate HBV precore/core protein.

The disruption of virus particles with a surfactant and the exposure (display) of the HBV precore protein are followed by the step of measuring with a probe that recognizes the HBV precore protein. By using a probe that recognizes an amino acid sequence at positions −28 to 150 in this step, the HBV precore protein can be measured. Any probe may be used as long as it binds to this precore protein, such as antibody, receptor, aptamer, ligand etc.

Assay methods may be any ones that utilize the binding of the HBV precore protein and the probe, and representative ones include enzyme-antibody immunological methods. In order to separately determine the HBV precore protein and HBc antigen, a probe that recognizes −28 to −11 may be used for the HBV precore protein and a probe that recognizes 151 to 183 may be used for the HBc antigen. However, it is also possible to determine the HBV precore protein by determining the combined amount of the HBV precore protein and the HBc antigen with a probe that recognizes 1-150 which is a common region, determining the amount of the HBc antigen with a probe that recognizes 151-183, and then subtracting it from the above combined amount.

EXAMPLES

The following Examples illustrate the present invention, but it should be noted that they do not limit the scope of the present invention in any way.

Example 1

Fractionation of the HBV Core-Related Antigens by Sucrose Density Gradient Centrifugation (A) Fractionation by 10-60% Sucrose Density Gradient Centrifugation To a TNE buffer [10 mM Tris-HCl, pH 7.5, 150 mM NaCl, 1 mM EDTA], sucrose is dissolved to 10%, 20%, 30%, 40%, 50%, and 60%, respectively, and starting with the higher density 60% sucrose solution, 1.7 ml each of the sucrose solution is sequentially layered in a 12 ml ultracentrifuge tube, which is allowed to stand for six hours at room temperature.

Figure 2:
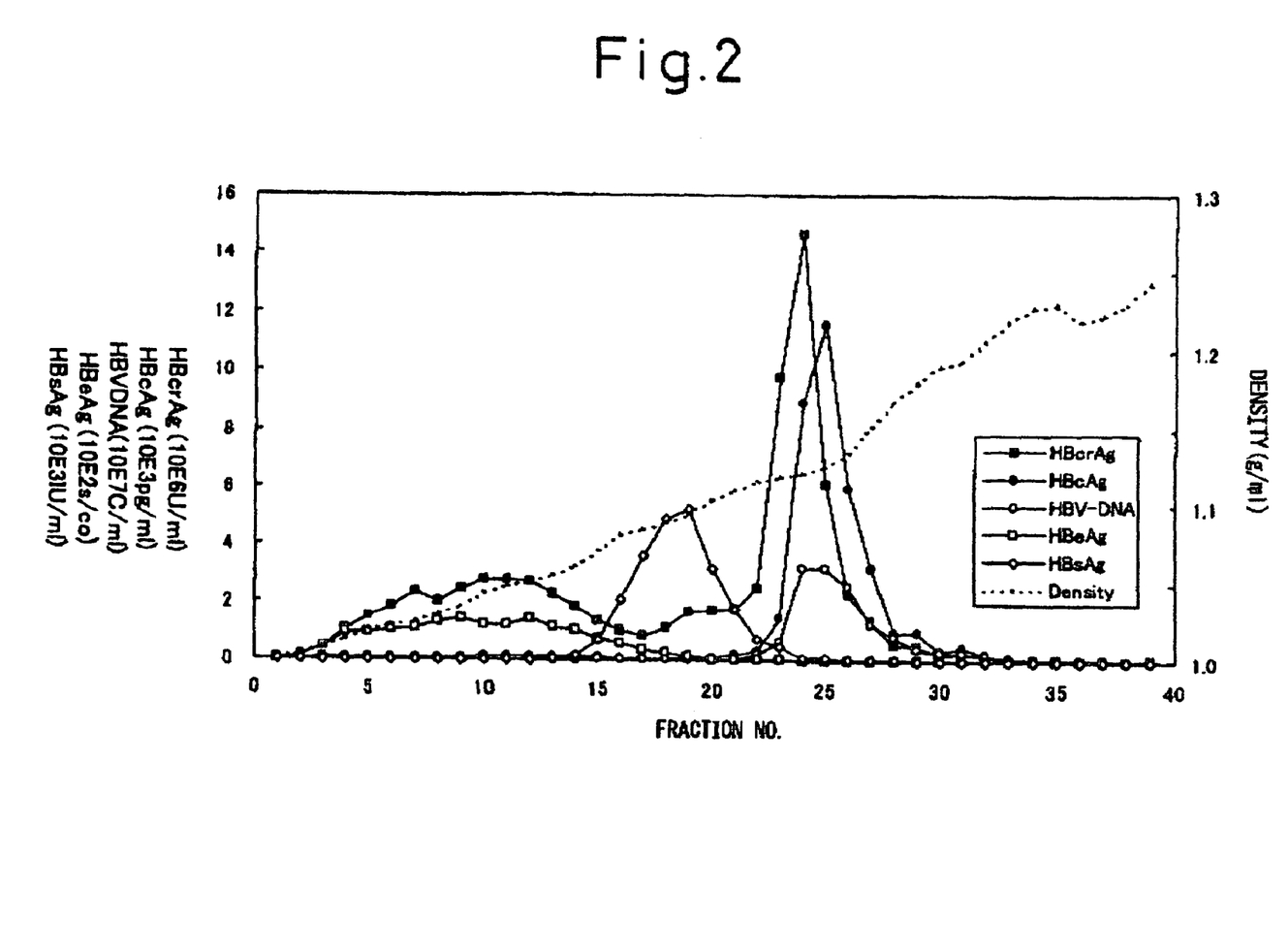
FIG. 2 is a drawing that shows behaviors of HBV antigen and HBV DNA of the HBe antigen-positive serum separated by the sucrose density gradient centrifugation. It shows HBV core-related antigens (black square), HBc antigen (Solid circle), HBs antigen (Open diamond), HBe antigen (Open square), and HBV DNA (Open circle) in each fraction, and the density of fractions is shown in a broken line.

One ml of the HBe antigen-positive serum is layered on the prepared sucrose density solution, and after centrifuging using the Sw40Ti rotor (Beckman) at 334,000 rpm, 4° C. for 15 hours, 300 µl each was taken from the top in 40 fractions. The density of each fraction was calculated, and the determination of the HBV core-related antigen (PCT application: PCT/JP01/06947), HBc antigen (PCT application: PCT/JP01/06947), HBs antigen (Dainabott), HBe antigen (Dainabott), and HBV-DNA PCR (Roche Diganostic) revealed that part of the HBV core-related antigen exhibited a peak at a density similar to that of the HBe antigen and most of the HBV core-related antigen was detected in the vicinity of the peak of the HBV-DNA PCR (FIG. 2).

(B) Refractionation by a Low-Gradient Sucrose Density Gradient Centrifugation

Figure 3:
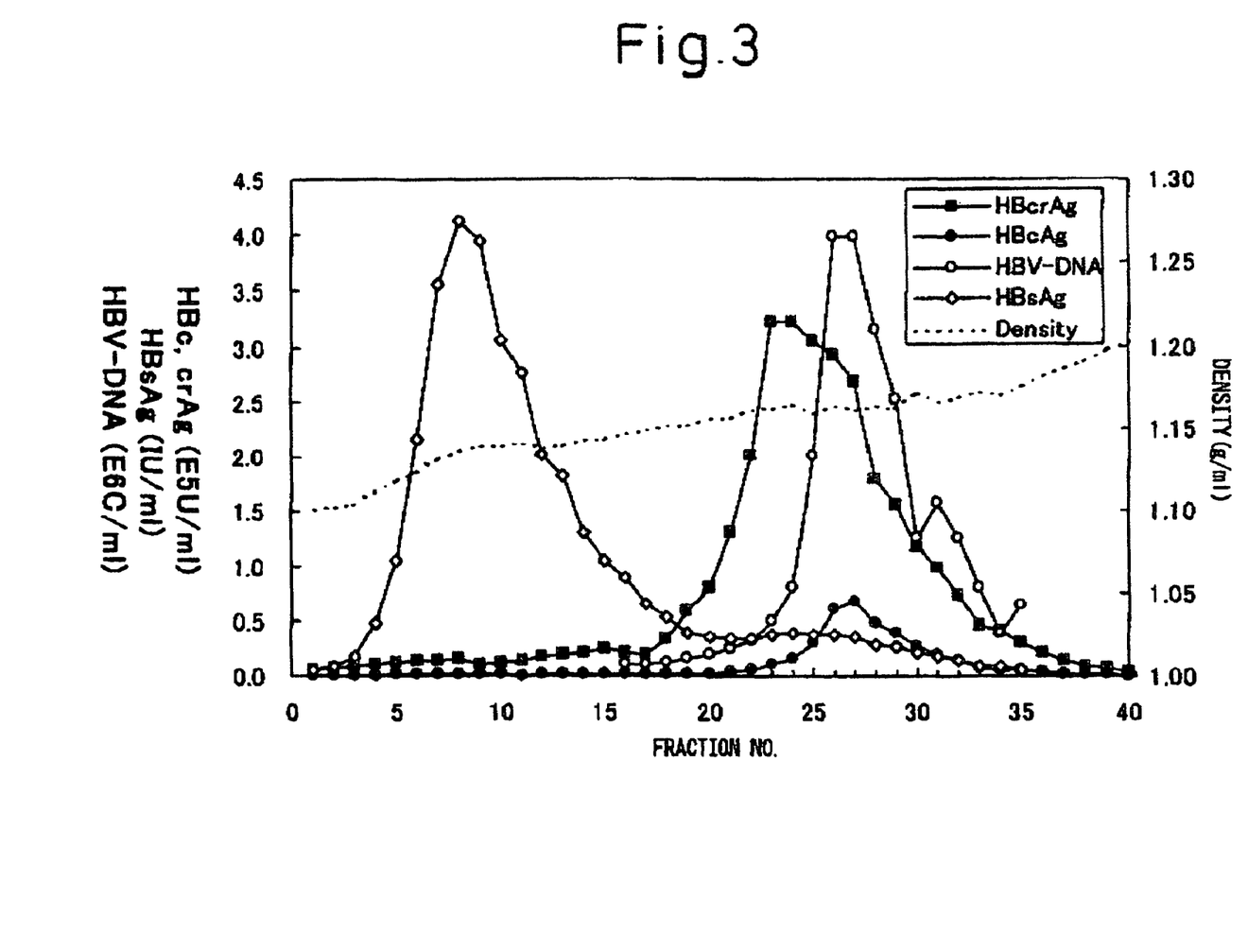
FIG. 3 is a drawing that shows behaviors of HBV antigen and HBV DNA when the peak fraction of the HBV core-related antigens separated by sucrose density gradient centrifugation was separated again by sucrose density gradient centrifugation. It shows HBV core-related antigens (black square), HBc antigen (Solid circle), HBs antigen (Open diamond), and HBV DNA (Open circle) in each fraction, and the density of fractions is shown in a broken line.

Starting with the higher density 50% sucrose solution, 3.4 ml each of the 30%, 40% and 50% sucrose solution sequentially is carefully layered in a 12 ml ultracentrifuge tube, which is allowed to stand for six hours at room temperature. (A) After the peak fractions at No. 24 and 25 were diluted two-fold with the TE buffer [10 mM Tris-HCl, pH 8.0, 1 mM EDTA], they were layered on the prepared sucrose density solution, and after centrifuging using the Sw40Ti rotor (Beckman) at 334,000 rpm, 4° C. for 15 hours, 300 µl each thereof was taken from the top in 40 fractions. The density of each fraction was calculated, and the determination of the HBV core-related antigen (PCT application: PCT/JP01/06947, Example 5), HBc antigen (PCT application: PCT/JP01/06947, Example 6), HBs antigen, and HBV-DNA PCR revealed that the peak of the HBV core-related antigen is located at a lower density fraction than that of HBV-DNA PCR and the fraction contained HBs antigen (FIG. 3). After dialysis, each fraction was stored at 4° C.

Example 2

Gel Filtration with the Nonidet P-40 Treatment

Figure 4:
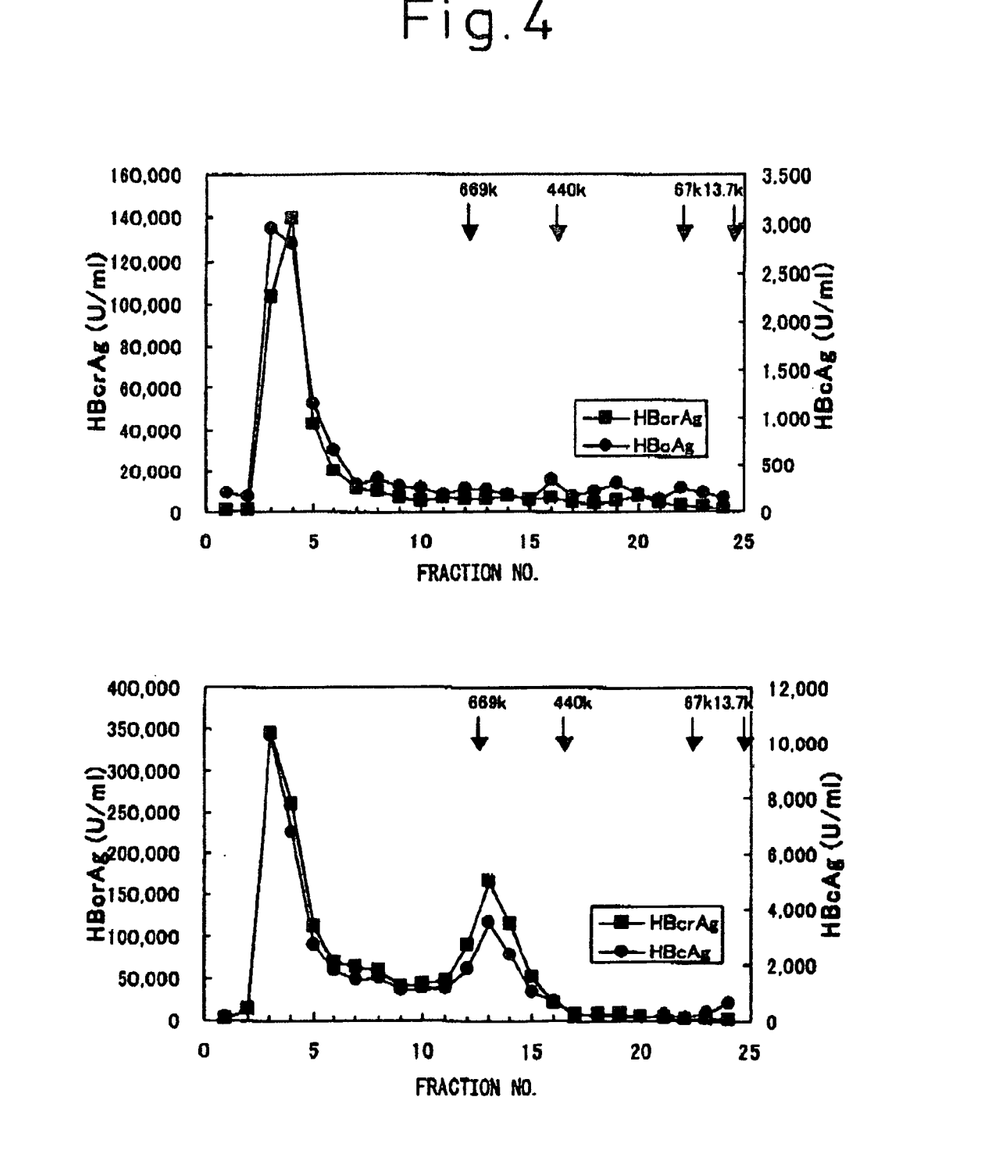
FIG. 4 is a drawing that shows the behaviors of HBV antigen in gel filtration. The upper figure: the peak fraction of HBV core-related antigens separated by sucrose density gradient centrifugation was gel-filtrated without any treatment. The bottom figure: the same sample was gel-filtrated after treatment with 3% NP-40. It shows HBV core-related antigens (black square) and HBc antigen (Solid circle) in each fraction. The positions where molecular weight markers are eluted are shown in the upper part.

When the peak fractions (Nos. 24-25) fractionated in the above Example 1(A) was gel-filtrated using the Superose 6 HR (Amersham) equilibrated with 10 mM phosphate buffer, pH 7.3, (PBS) containing 0.15 M NaCl, the HBV core-related antigen and the HBc antigen were each eluted at the void fraction (FIG. 4, upper figure). On the other hand, NP-40 was added to the peak fractions (Nos. 24-25) fractionated in the above Example 1(A) to a final concentration of 3% and was treated at 37° C. for 15 minutes to peel off the HBs antigen.

When this was gel-filtrated using the Superose 6 HR (Amersham) equilibrated with 10 mM phosphate buffer, pH 7.3, (PBS) containing 0.15 M NaCl, naked particles containing the HBV core-related antigen or the HBc antigen were each eluted at the void fraction (FIG. 4, lower figure). Since the molecular weight of the void fraction of the Superose 6 HR is 40,000,000 or over, these molecule are thought to have a virus capsid-like particle structure.

Example 3

Analysis by the Western Blot Method

Figure 5:
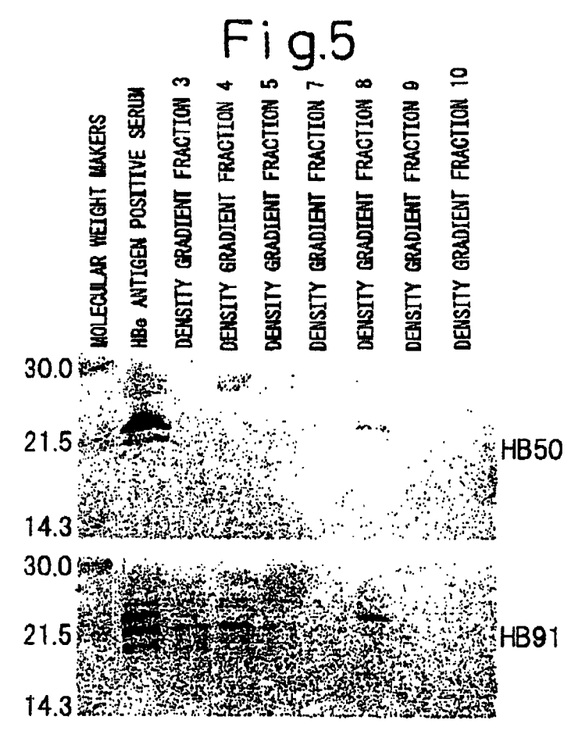
FIG. 5 is an electrophoretogram that shows the result of Western blot analysis on the HBe antigen-positive serum and the density gradient centrifuged fractions, and a photograph substituted for drawings. Fractions 1-20 from density gradient centrifugation correspond to the sucrose concentration of 10-60%. HB50 is a monoclonal antibody that only reacts to HBc antigen, and HB91 is a monoclonal antibody that reacts to both of HBc antigen and HBe antigen.

In a similar manner to that described in Example 1(A), the HBe antigen-positive serum was subjected to sucrose density gradient centrifugation, and 20 fractions of 600 μl each were taken from the supernatant. The fractions and the HBe antigen-positive serum were subjected to SDS-PAGE, transferred to a PVDF membrane (Immobilon, Millipore), and then by Western blot using a monoclonal antibody HB91 that recognizes both of the HBc antigen and the HBe antigen and a monoclonal antibody HB50 that is specific for the C-terminal nucleic acid-binding region, the HBV core-related antigen with a molecular weight of about 22,000 Daltons was detected (FIG. 5, upper figure). It was also demonstrated that this HBV core-related antigen reacts to HB91 but not to HB50 (FIG. 5, bottom figure).

By epitope analysis, the HB50 antibody has been demonstrated to recognize amino acids (SQSPRRRRS; SEQ ID NO: 8) at positions 168-176, and in addition, it has also been found to react to a peptide (STLPETTVVRRRGRSPRRR; SEQ ID NO: 9) at positions 141-159 and a peptide (RRRGRSPRRRTPSPRRRR; SEQ ID NO: 10) at positions 150-167. The common sequence of these peptide is SPRRR (SEQ ID NO: 7), and at least this sequence is required for binding to the HB50 antibody. Thus, as this SPRRR (SEQ ID NO: 7) sequence is located at position 155 or after, the HBV precore/core protein of the present invention is likely to lack the sequence at position 155 or after. This is also clear from the fact that a peak in the HBc antigen assay system that uses HB50 antibody alone as a labelled antibody does not superimpose on the peak of the HBV precore/core protein (FIG. 2, FIG. 3).

Example 4

Analysis of Amino Acid Sequence by MALDI Mass Spectrometry

When the HBV core-related antigen fractions obtained in the Example 1(A) was gel-filtrated using the Superose 6 HR (Amersham) equilibrated with 10 mM phosphate buffer, pH 7.3, (PBS) containing 0.15 M NaCl, particles comprising the HBV core-related antigen and the HBc antigen were eluted at the void fraction. These void fractions were layered on the TNE buffer [10 mM Tris-HCl, pH 7.5, 150 mM NaCl, 1 mM EDTA] containing 1% NP-40 and 20% sucrose, and after centrifuging using the Sw40Ti rotor (Beckman) at 334,000 rpm, 4° C. for 15 hours, pellets containing the HBV core-related antigen particles were recovered.

The pellets were separated on SDS-PAGE, a 22 kDa band of the HBV core-related antigen was excised, and after trypsin digestion, it was subjected to MALDI-TOF mass spectrometry by the Voyager-DE STR (Applied Biosystems).

As a result, five peptides corresponding to the sequences as set forth in SEQ ID NO: 2, 3, 4, 5 and 6 were detected. Among them, the peptide of SEQ ID NO: 2 was acetylated at the N-terminal.

Example 5

The Detection and Assay Method of HBV Core-Related Antigen (Precore/core Protein)

Anti-HBV core antigen monoclonal antibody HB44 (recognition site: amino acids at 31-49), HB61 (recognition site: amino acids at 131-140) and HB114 (recognition site: amino acids at 1-81) were diluted to a final concentration of 2, 1 and 1 μg/ml, respectively, in 0.5 M NaCl carbonate buffer, pH 9.6, and dispensed into a black 96-well microtiter plate (Nunc) at 100 μl/well, and then allowed to stand overnight at 4° C. After washing twice with 0.4 ml of 10 mM phosphate buffer, pH 7.4, containing 0.15 M NaCl, 0.4 ml of the blocking solution (0.5% sodium casein, 3% sucrose, 150 mM NaCl, 10 mM phosphate buffer, pH 7.4) was added thereto, and the plate was allowed to stand at room temperature for two hours. After discarding the blocking solution, it was dried under vacuum.

To 100 μl of the serum, 50 μl of the treating solution (15% SDS, 2% Tween 60) was added, and treated at 70° C. for 30 minutes, 50 μl of which was used as the sample for measurement.

To the above well, 100 μl of the reaction buffer and 50 μl of the sample were added, and were allowed to react at room temperature for two hours.

After washing five times with 0.4 ml of the washing solution (0.05% Tween 20, 0.15 M NaCl, 10 mM phosphate buffer, pH 7.4), alkaline phosphatase (AP)-labelled monoclonal antibody HB91 (recognition site: amino acids at 1-19) and HB110 (recognition site: amino acids at 21-40) that were diluted to 0.1 μg/ml and 0.5 μg/ml, respectively, which were added at 100 μl/well, and were allowed to react at room temperature for one hour. After washing six times with 0.4 ml of the washing solution, 100 μl of the CDP-Star with Emerald II (TROPIX) solution as the luminescence substrate was allowed to react at room temperature for 20 minutes, and then the luminescence was measured.

Example 6

Determination of HBc Antigen (A) Preparation of the Antibody-Immobilized Plate

Three types of monoclonal antibodies HB44 (recognition site: amino acids at 31-49), HB61 (recognition site: amino acids at 131-140) and HB114 (recognition site: amino acids at 1-81) that react to both HBc antigen and HBe antigen were sensitized to microtiter plate wells and immobilized. After washing with PBS, they were blocked with a casein-containing solution and, after removing this solution, they were dried.

(B) Pretreatment of Samples

Fifty μl of the pretreatment solution (15% sodium dodecyl sulfate [SDS], 3% CHAPS, 1% hexadecyltrimethyl ammonium bromide) and 100 μl of the sample (serum, plasma etc.) were mixed and treated at 70° C. for 30 minutes.

(C) Primary Reaction

To each antibody-immobilized well, 100 μl of the reaction buffer (pH8.0) and 50 μl of the pretreated sample were added, and under gentle stirring it was allowed to react at room temperature for two hours.

(D) Secondary Reaction

After washing the wells, 100 μl of a solution containing alkaline phosphatase-labelled HB50 (recognition site: amino acids at 168-176) monoclonal antibody was added and was allowed to react at room temperature for one hour.

(E) Substrate Reaction

After washing the wells, 100 μl of the CDP-Star with Emerald II (Applied Biosystems) solution was added, and after reacting for 20 minutes, the amount of luminescence in each well was measured using a microplate luminometer.

Example 7

Determination of HBV Precore Protein, HBe Antigen and HBc Antigen in the Sample and the Calculation of their Ratio According to the method in the above Example 1(A), seven serum samples were fractionated by sucrose density gradient centrifugation. Each sample was divided into the fraction (in FIG. 1, for example, fractions Nos. about 1-19) containing the low-density free HBe antigen and the fraction (in FIG. 1, for example, fractions No. 20 or greater) containing the high-density virus particles, and their antigens were determined by the methods in Example 5 and Example 6.

When the low-density fraction is determined by the method in Example 5, free HBe antigen containing no virus particles is determined in this fraction. Also when the high-density fraction is determined by the method in Example 5, this assay method measures both HBc antigen and particulate precore protein combined, and therefore by subtracting the value in Example 6 from the that determined in Example 5, the value of particulate HBV precore protein can be calculated. The ratio of thus determined and calculated HBe antigen, HBc antigen and HBV precore protein in each sample was calculated (Table

TABLE 1

| Sample | HBV precore protein/HBe antigen | HBV precore protein/HBc antigen |
|---|---|---|
| BBI PHM935A-14 | 13.437 | 27.236 |
| BBI PHM935A-16 | 6.321 | 158.352 |
| BBI PHJ201-04 | 0.589 | 22.070 |
| BBI PHJ201-07 | 1.367 | 44.853 |
| BBI PHJ201-13 | 0.296 | 33.743 |
| ProMedDex#101499 | 0.025 | 12.031 |
| ProMedDex#999077 | 1.653 | 12.779 |
| Mean | 3.384 | 44.438 |

HBV precore protein : HBe antigen is 13:1 to 1:40, and some samples contain one more than the other. On the other hand, HBV precore protein : HBc antigen is in the range of 12:1 to 158:1, and all samples contain more HBV precore protein.

TABLE 2

Differential determination of HBe antigen, HBc antigen and particulate HBV precore protein by density gradient centrifugation

| | HBc antigen | | | HBV precore/core protein | | | Particulate precore protein | |
|---|---|---|---|---|---|---|---|---|
| Sample name | Low density A pg/ml | High density B pg/ml | High density ratio B/(A + B) % | Low density C pg/ml | High density D pg/ml | High density ratio D/(C + D) % | E = D − B pg/ml | Ratio E/(C + D) % |
| BBI PHM901-06 | | | | 809 | 1,038 | 56% | 1,038 | 56% |
| BBI PHM907-10 | | | | 22,735 | 2,297 | 9% | 2,297 | 9% |
| BBI PHM921-06 | | | | 1,436 | 1,410 | 50% | 1,410 | 50% |
| BBI PHM922-12 | 100 | 902 | 90% | 12,977 | 9,910 | 43% | 9,007 | 39% |
| BCP HBV6278-11 | 672 | 137,407 | 100% | 2,217,048. | 1,027,110 | 32% | 889,703 | 27% |
| Nabi SB0408-J | 3,066 | 164,303 | 98% | 753,697 | 1,771,119 | 70% | 1,606,816 | 64% |
| BBI PHM935A-14 | 1,685 | 171,323 | 99% | 291,285 | 4,690,058 | 94% | 4,518,735 | 91% |
| BBI PHM935A-16 | 107 | 3,511 | 97% | 63,713 | 573,768 | 90% | 570,257 | 89% |
| ProMedDx #9990776 | 1,921 | 63,059 | 97% | 487,502 | 805,856 | 62% | 742,797 | 57% |
| ProMedDx #10149975 | 117 | 3,605 | 97% | 1,708,934 | 43,372 | 2% | 39,767 | 2% |
| 01 1670 | 3,199 | 105,916 | 97% | 226,685 | 137,038 | 38% | 31,122 | 9% |
| 01 1351 | 98 | 13,630 | 99% | 768,967 | 351,768 | 31% | 338,138 | 30% |
| 01 3567 | 539 | 22,518 | 98% | 1,639,314 | 354,521 | 18% | 332,004 | 17% |
| 01 2296 | 31 | 2,172 | 99% | 386,067 | 36,338 | 9% | 34,166 | 8% |
| 01 1188 | 12 | 578 | 98% | 1,393 | 2,088 | 60% | 1,509 | 43% |
| 01 2877 | 108 | 4,863 | 98% | 79,403 | 72,987 | 48% | 68,124 | 45% |

Table 2 shows the determined values of HBc antigen, HBV core-related antigen and the concentration of particulate precore protein calculated therefrom in each fraction. In all samples that could be determined, 90% or more of the HBc antigen occurred in the high-density fraction. The HBV precore/core protein present in the low-density fraction is HBe antigen, and HBV precore/core protein in the high-density fraction is HBc antigen and particulate HBV precore protein. Thus, by subtracting the HBc antigen concentration from the concentration of the high-density HBV precore/core protein, the concentration of particulate precore protein can be calculated.

Example 8

Differential Determination of Free and Particulate HBV Precore/Core Protein and HBc Antigen and their Ratio in the Sample Fifty μl of the "Reaction Buffer", 50 μl of the "HBV supplement particles" (anti-HBs antibody-immobilized magnetic beads) in the HBV Direct-Mag kit (JSR K.K.) and 200 µl of the sample were mixed and shaken at room temperature for 30 minutes to effect the binding of HBV-related particles containing HBs antigen. The magnetic beads were separated by a powerful magnet and the supernatant was removed. The supernatant contains free HBe antigen. To the remaining magnetic beads, 60 µl of 15% SDS solution was added, and heated to 70° C. for 10 minutes to elute the bound particulate HBV precore/core protein. The magnetic beads were separated by a powerful magnet and the extract was removed.

Figure 6:
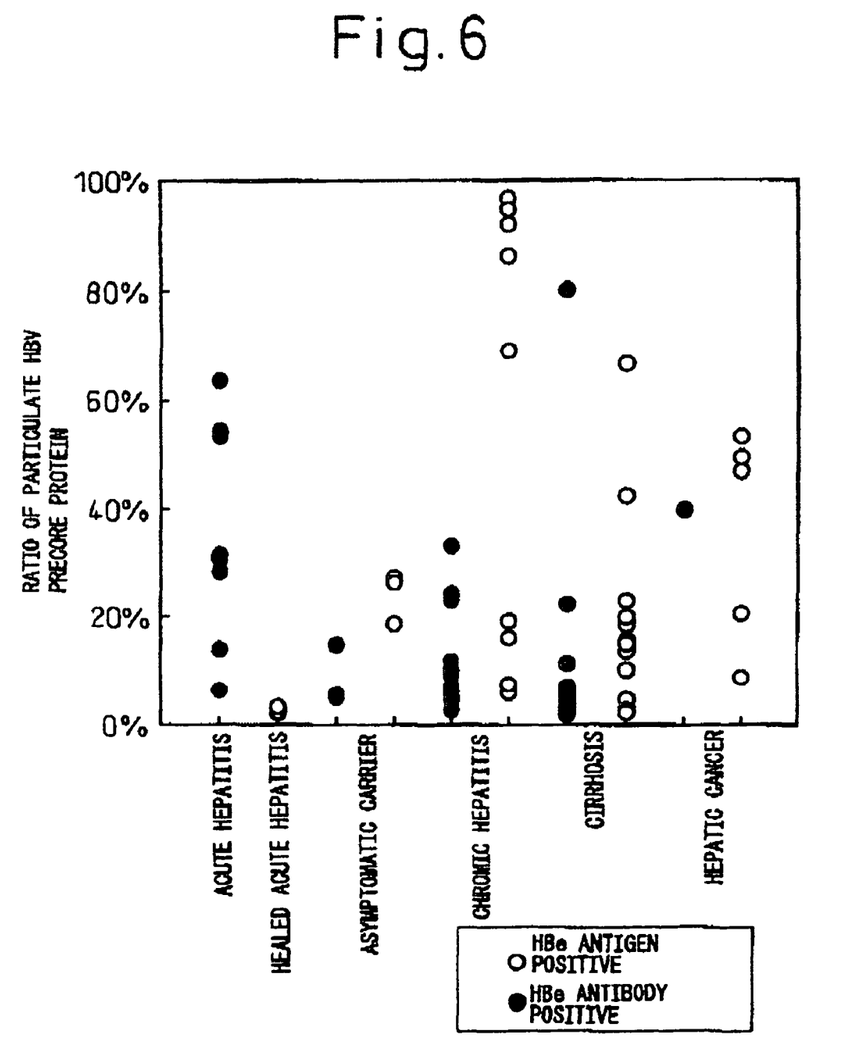
FIG. 6 is a drawing that shows the ratio of the particulate precore protein to total precore/core protein in each case. HBe antigen-positive cases are shown in (Solid circle) and HBe antibody-positive cases in (Open circle).

The HBV precore/core protein and HBcAg in the supernatant and the precipitate were determined by the methods in Example 5 and Example 6, and the concentrations and ratio of HBe antigen, HBc antigen and the particulate HBV precore protein in the sample were calculated. The result is shown in Table 3.

similar to Example 8, free and particulate HBV precore/core protein and HBc antigen were differentially determined to compare the ratio of the particulate HBV precore protein to the total precore/core protein (HBe antigen+HBc antigen+ particulate HBV precore protein). The result is shown in FIG. 6.

In HBe antigen-positive cases, it tends to be higher in acute hepatitis and lower in asymptomatic carriers and cirrhosis. Also, in HBe antibody-positive cases, it tends to be higher in chronic hepatitis and hepatic cancer and lower in healed acute hepatitis and cirrhosis. These results indicate that the determination of the particulate precore protein provides useful findings on the diagnosis and treatment of type B hepatitis, and further serves to elucidate the pathology of HBV and type

TABLE 3

Differential determination of HBe antigen, HBc antigen and particulate HBV precore protein by immunoprecipitation with HBs antibody

| | HBc antigen | | | HBV precore/core protein | | | Particulate precore protein | |
|---|---|---|---|---|---|---|---|---|
| Sample name | Supernatant A pg/ml | Precipitate B pg/ml | Precipitation ratio B/(A + B) % | Supernatant C pg/ml | Precipitate D pg/ml | Precipitation ratio D/(C + D) % | E = D − B pg/ml | Ratio E/(C + D) % |
| BBI PHM901-06 | 5 | 69 | 93% | 2,151 | 948 | 31% | 879 | 28% |
| BBI PHM907-10 | 5 | 207 | 98% | 29,728 | 2,219 | 7% | 2,012 | 6% |
| BBI PHM921-06 | 3 | 76 | 96% | 2,723 | 1,307 | 32% | 1,231 | 31% |
| BBI PHM922-12 | 46 | 749 | 94% | 20,025 | 10,364 | 34% | 9,615 | 32% |
| BCP HBV6278-11 | 5,238 | 118,840 | 96% | 4,958,186 | 941,077 | 16% | 822,237 | 14% |
| Nabi SB0408-J | 4,296 | 116,834 | 96% | 1,382,054 | 1,829,461 | 57% | 1,712,627 | 53% |
| BBI PHM935A-14 | 8,671 | 188,535 | 96% | 1,636,481 | 3,370,973 | 67% | 3,182,438 | 64% |
| BBI PHM935A-16 | 959 | 7,800 | 89% | 482,713 | 591,319 | 55% | 583,519 | 54% |
| ProMedDx #9990776 | 6,264 | 52,270 | 89% | 1,646,640 | 1,184,289 | 42% | 1,132,020 | 40% |
| ProMedDx #10149975 | 477 | 4,522 | 90% | 2,094,278 | 146,459 | 7% | 141,937 | 6% |
| 01 1670 | 2,877 | 137,930 | 98% | 540,397 | 177,755 | 25% | 39,825 | 6% |
| 01 1351 | 535 | 32,615 | 98% | 2,168,349 | 414,203 | 16% | 381,588 | 15% |
| 01 3567 | 1,409 | 40,800 | 97% | 5,325,365 | 325,486 | 6% | 284,686 | 5% |
| 01 2296 | 198 | 5,319 | 96% | 1,036,210 | 59,531 | 5% | 54,212 | 5% |
| 01 1188 | 23 | 692 | 97% | 5,171 | 2,151 | 29% | 1,460 | 20% |
| 01 2877 | 555 | 11,692 | 95% | 161,907 | 126,510 | 44% | 114,818 | 40% |

In all samples that could be determined, 90% or more of the HBc antigen occurred in the precipitate. Thus, almost all of the particles covered with HBs antigen are immunoprecipitated. The HBV precore/core protein present in the supernatant is HBe antigen, and the HBV precore/core protein in the precipitate is HBc antigen and particulate HBV precore protein. Therefore, by subtracting the HBc antigen concentration from the concentration of particulate precore protein in the precipitate, the particulate precore protein concentration can be calculated. This concentration and the ratio are very similar to the result of differential determination by density gradient centrifugation shown in Example 7, indicating that the differential determination of the particulate precore protein can be performed by both methods.

Example 9

Difference in the Ratio of Particulate HBV Precore Protein by Pathological Conditions For 81 serum samples from HBV carriers and various pathological conditions such as type B hepatitis, in a manner B hepatitis. Through these findings, useful findings for the development of therapeutic agents for type B hepatitis could be obtained.

Example 10

Comparison of Methods for Sample Treatment

Various solutions for pretreatment of samples were prepared, and by only changing the pretreatment solutions as in Example 6, five samples of HBV-positive serum were subjected to sample treatment and HBc antigen determination to compare the effects of each treatment method.

Among them, SDS, N-lauroyl sarcosine-Na, deoxycholic acid-Na are anionic surfactants, and n-decyl trimethyl ammonium-Br is a cationic surfactant. The final concentration of each surfactant during sample treatment becomes ⅓ that in the pretreatment solution, and the final concentration during the primary reaction in the HBc antigen assay system becomes ⅑.

TABLE 4

Reaction (amount of luminescence) by HBc antigen ELISA in each treatment method

| Pretreatment solution | None | 15% SDS | 15% N-Lauroyl sarcosine-Na | 7.5% Deoxycholic acid-Na | 15% n-Decyl trimethyl ammonium-Br |
|---|---|---|---|---|---|
| Negative | 180 | 154 | 158 | 156 | 503 |
| Sample 1 | 364 | 46656 | 4208 | 1375 | 1381 |
| Sample 2 | 212 | 4249 | 510 | 459 | 357 |
| Sample 3 | 151 | 2157 | 1323 | 141 | 311 |
| Sample 4 | 167 | 2487 | 430 | 143 | 292 |
| Sample 5 | 153 | 1609 | 300 | 180 | 378 |

The result revealed that anionic surfactants such as SDS, N-lauroyl sarcosine-Na and deoxycholic acid-Na are suitable as the treatment solution. Among them, SDS is most suitable. On the other hand, the use of cationic surfactants alone such as n-decyl trimethyl ammonium-Br leads to high background in the negative samples, and thus is not suitable for this assay system (Table 4).

TABLE 5

Reaction (amount of luminescence) by HBc antigen ELISA in each treatment method

| | Pretreatment solution | | |
|---|---|---|---|
| | 15% SDS | 15% SDS, 1.5% CHAPS | 15% SDS, 1.5% CHAPS 0.3% Triton X-100 |
| Negative | 29 | 26 | 42 |
| Sample 1 | 35009 | 45368 | 50818 |
| Sample 2 | 2323 | 3739 | 4316 |
| Sample 3 | 541 | 903 | 1046 |
| Sample 4 | 1327 | 2048 | 2158 |
| Sample 5 | 532 | 690 | 773 |

The result revealed that by adding CHAPS, an ampholytic surfactant, or Triton X-100, a nonionic surfactant, etc. in addition to 15% SDS as the pretreatment solution, the effect of pretreatment is further enhanced (Table 5).

Example 11

Antigenicity of Particulate HBV Precore Protein

Anti-HBc monoclonal antibody (Anti-HBc (β) 2A22 Institute of Immunology) was diluted to 1 μg/ml with 0.5 M NaCl, 0.1M carbonate-Na buffer, pH 9.6, dispensed at 100 μl/well to a 96-well microtiter plate (Nunc), and then allowed to stand overnight at 4° C. After washing with PBS, it was blocked with a casein-containing solution. After removing this solution, the sample solution was added at 100 μl/well, and was allowed to react at room temperature for one hour. It was washed with the washing solution, and then 1 μg/ml of biotin-labelled 2A22 monoclonal antibody was added at 100 μl/well, and was allowed to react at room temperature for one hour. After washing with the washing solution, 10,000-fold diluted peroxidase-labelled avidin (Vector) was added at 100 μl/well, and was allowed to react at room temperature for one hour. After washing with a washing solution, an aqueous solution of OPD (Sigma)/hydrogen peroxide was added at 100 μl/well, and was allowed to develop color at room temperature for 30 minutes. After adding 1 M sulfuric acid at 100 μl/well to stop the reaction, absorbance at 420nm was measured.

In this assay system, about 2 ng/ml of HBcAg could be detected. After removing the envelop by treating the peak fraction of the HBV core-related antigen in Example 1(A) with 1% NP-40, it was diluted 10-fold (the content of the HBV core-related antigen is about 150 ng/ml) and was subjected to the above measurement, but no HBc antigen was detected.

The same sample was measured by the HBe antigen assay system (Dainabott) that is in clinical use, but no HBe antigen was detected either. Thus, the particulate HBV precore protein of the present invention is believed to have an antigenicity different from those of HBc antigen and HBe antigen.

The invention claimed is:

1. A method of determining the presence of an HBV precore protein that has an ability of forming the core-like particles of HBV and that contains all or part of the signal sequence, wherein the HBV precore comprises the amino acid sequence shown in SEQ ID NO: 1, the method comprising:
   (1) exposing the HBV precore protein to a surfactant;
   (2) contacting the HBV precore protein with a probe that recognizes the HBV precore protein; and
   (3) detecting binding of the HBV precore protein to the probe that recognizes the HBV precore protein,
wherein the binding to a probe that recognizes the HBV precore protein indicates the presence of the HBV precore protein.

2. The method according to claim 1 wherein said surfactant is any of an anionic surfactant, an anionic surfactant and an ampholytic surfactant, or an anionic surfactant, an ampholytic surfactant and a nonionic surfactant.

3. The method according to claim 1 wherein said probe that binds to the HBV precore protein is a probe that binds to the positions 1 to 18 of the amino acid sequence shown in SEQ ID NO: 1, or a probe that specifically binds to the HBV precore protein comprising the amino acid sequence shown in SEQ ID NO: 1, but does not bind to HBe antigen or HBc antigen.

4. The method according to claim 3 wherein said probe that binds to the HBV precore protein comprises at least one antibody.

5. The method according to claim 4 wherein said probe that binds to the HBV precore protein is a combination of two or more of antibodies that recognize positions 29 to 47 in the amino acid sequence shown in SEQ ID NO: 1, an antibody that recognizes positions 49 to 68 in the amino acid sequence shown in SEQ ID NO: 1, an antibody that recognizes positions 59 to 77 in the amino acid sequence shown in SEQ ID NO: 1, an antibody that recognizes positions 158 to 168, and an antibody that recognizes the structural region of positions 29 to 109 in the amino acid sequence shown in SEQ ID NO: 1.

* * * * *

SEQUENCE LISTING

<160> NUMBER OF SEQ ID NOS: 10

<210> SEQ ID NO 1
<211> LENGTH: 178
<212> TYPE: PRT
<213> ORGANISM: Hepatitis B virus
<220> FEATURE:
<223> OTHER INFORMATION: hepatitis B virus core protein

<400> SEQUENCE: 1

```
Gln Leu Phe His Leu Cys Leu Ile Ile Ser Cys Ser Cys Pro Thr Val
  1               5                  10                  15

Gln Ala Ser Lys Leu Cys Leu Gly Trp Leu Trp Gly Met Asp Ile Asp
             20                  25                  30

Pro Tyr Lys Glu Phe Gly Ala Ser Val Glu Leu Leu Ser Phe Leu Pro
         35                  40                  45

Ser Asp Phe Phe Pro Ser Ile Arg Asp Leu Leu Asp Thr Ala Ser Ala
     50                  55                  60

Leu Tyr Arg Glu Ala Leu Glu Ser Pro Glu His Cys Ser Pro His His
 65                  70                  75                  80

Thr Ala Leu Arg Gln Ala Ile Leu Cys Trp Gly Glu Leu Met Asn Leu
```

```
                85                  90                  95
Ala Thr Trp Val Gly Ser Asn Leu Glu Asp Pro Ala Ser Arg Glu Leu
            100                 105                 110

Val Val Ser Tyr Val Asn Thr Asn Met Gly Leu Lys Ile Arg Gln Leu
            115                 120                 125

Leu Trp Phe His Ile Ser Cys Leu Thr Phe Gly Arg Glu Thr Val Leu
            130                 135                 140

Glu Tyr Leu Val Ser Phe Gly Val Trp Ile Arg Thr Pro Pro Ala Tyr
145                 150                 155                 160

Arg Pro Pro Asn Ala Pro Ile Leu Ser Thr Leu Pro Glu Thr Thr Val
                165                 170                 175

Val Arg

<210> SEQ ID NO 2
<211> LENGTH: 20
<212> TYPE: PRT
<213> ORGANISM: Hepatitis B virus
<220> FEATURE:
<223> OTHER INFORMATION: part of hepatitis B virus core protein

<400> SEQUENCE: 2

Gln Leu Phe His Leu Cys Leu Ile Ile Ser Cys Ser Cys Pro Thr Val
1               5                   10                  15

Gln Ala Ser Lys
            20

<210> SEQ ID NO 3
<211> LENGTH: 11
<212> TYPE: PRT
<213> ORGANISM: Hepatitis B virus
<220> FEATURE:
<223> OTHER INFORMATION: part of hepatitis B virus core protein

<400> SEQUENCE: 3

Asp Leu Leu Asp Thr Ala Ser Ala Leu Tyr Arg
1               5                   10

<210> SEQ ID NO 4
<211> LENGTH: 17
<212> TYPE: PRT
<213> ORGANISM: Hepatitis B virus
<220> FEATURE:
<223> OTHER INFORMATION: part of hepatitis B virus core protein

<400> SEQUENCE: 4

Glu Ala Leu Glu Ser Pro Glu His Cys Ser Pro His His Thr Ala Leu
1               5                   10                  15

Arg

<210> SEQ ID NO 5
<211> LENGTH: 14
<212> TYPE: PRT
<213> ORGANISM: Hepatitis B virus
<220> FEATURE:
<223> OTHER INFORMATION: part of hepatitis B virus core protein

<400> SEQUENCE: 5

Glu Leu Val Val Ser Tyr Val Asn Thr Asn Met Gly Leu Lys
1               5                   10

<210> SEQ ID NO 6
<211> LENGTH: 23
<212> TYPE: PRT
```

```
<213> ORGANISM: Hepatitis B virus
<220> FEATURE:
<223> OTHER INFORMATION: part of hepatitis B virus core protein

<400> SEQUENCE: 6

Thr Pro Pro Ala Tyr Arg Pro Pro Asn Ala Pro Ile Leu Ser Thr Leu
 1               5                  10                  15

Pro Glu Thr Thr Val Val Arg
            20

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Pro Arg Arg Arg
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Ser Pro Arg Arg Arg Ser
 1               5

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Thr Leu Pro Glu Thr Thr Val Val Arg Arg Arg Gly Arg Ser Pro
 1               5                  10                  15

Arg Arg Arg

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Arg Gly Arg Ser Pro Arg Arg Arg Thr Pro Ser Pro Arg Arg
 1               5                  10                  15

Arg Arg
```